United States Patent [19]

Kirmann

[11] Patent Number: Plant 6,080

[45] Date of Patent: Jan. 12, 1988

[54] GERANIUM PLANT NAMED MICKY

[75] Inventor: Wolfgang Kirmann, Langenzersdorf, Austria

[73] Assignee: Mirko Vavra, Bisamberg, Austria

[21] Appl. No.: 811,115

[22] Filed: Dec. 19, 1985

[51] Int. Cl.[4] ..... A01H 5/00
[52] U.S. Cl. ..... Plt./68
[58] Field of Search ..... Plt. 68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Micky having bright red-purple flower color with a much deeper red-purple variegation on the upper two petals and approximate center of lower petals; medium early flowering; good bud production at night temperatures up to 16° C., thus providing a long and continuous flowering period; very compact, self-branching growth habit; good resistance against white fly; and ease of propagation and rooting habit.

2 Drawing Figures

The present invention comprises a new and distinct cultivar of geranium, botanically known as *Pelargonium domesticum*, and hereinfter referred to by the cultivar name Micky.

Micky is a product of a planned breeding program which had the objective of creating new geranium cultivars having compact growth habit, excellent flower production, long flowering period, small foliage, and bright red-purple flower color.

Micky was originated from a hybridization made by applicant in a controlled breeding program in Bisamberg, Austria in 1975. The female parent was Piroschka, a lilac sport of Fruhling. The male parent of Micky was a cultivar designated as seedling 14/73 characterized by its very compact growth habit and small, dark purple flowers.

Micky was discovered and selected as one flowering plant within the progeny of the stated cross by applicant on Apr. 14, 1976 in a controlled environment in Bisamberg, Austria.

The first act of asexual reproduction of Micky was accomplished when vegetative cuttings were taken from the initial selection on Aug. 21, 1976 in a controlled environment in Bisamberg, Austria by a technician working under formulations established and supervised by Wolfgang Kirmann. Horticultural examination of selected units initiated in the spring of 1977 has demonstrated that the combination of characteristics as herein disclosed for Micky are firmly fixed and are retained through successive generations of asexual reproduction.

Micky has not been observed under all possible environmental conditions. The phenotype may vary significantly with variations in environment such as temperature, light intensity, and day length. The following observations, measurements and comparisons describe plants grown in Bisamburg, Austria under conditions which approximate those generally used in commercial practice.

The following traits have been repeatedly observed and are determined to be basic characteristics of Micky, which in combination distinguish this geranium as a new and distinct cultivar.

1. A totally new bright red-purple flower color, variegated with dark red-purple on upper petals and at approximate center of lower petals.

2. Medium early flowering and long flowering period.

3. Very compact, self-branching growth habit, resulting in the setting of many buds.

4. Good resistance to parasites, particularly white fly.

5. Propagates well, with good rooting habit.

6. Good tolerance to inadvertent overwatering.

7. Buds are produced under normal greenhouse conditions (5000 Lux for 16 hours per day) at 14°-26° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.

8. Micky is unique with regard to the combined features of compactness, continuous flowering, floriferous habit, and red-purple flower color.

Of the many commercial cultivars known to the present inventor, the most similar in comparison to Micky is Piroschka, an unpatented but commercial cultivar. In comparison to Piroschka, Micky has a more compact growth habit, better flower production, and a more intense color.

The accompanying photographic drawings show typical flower and foliage characteristics of Micky, with colors being as true as possible with illustrations of this type.

Sheet 1 is a perspective view of a potted plant of Micky.

Sheet 2 is a black and white print showing the upper surface of immature and mature plants of Micky.

In the following description color references are made to The Royal Horticultural Society Colour Chart (R.H.S.). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Micky.

INFLORESCENCE

A. Umbel:
*Average diameter.*—Relatively small, 85–95 mm.
*Peduncle length.*—Normal.
*Pedicel length.*—Normal.

B. Corolla:
*Average diameter.*—55–65 mm; total inflorescence diameter is within the foliage.
*Form.*—Five-seven petals.
*Color (general tonality from a distance of three meters).*—Bright red-purple with deeper and more intense red-purple on upper petals and at approximate center of lower petals.
*Color (upper surface).*67C; center of lower petals and upper petals variegated with 61B and 59A.

C. Bud:
*Shape.*—Elongated.
*Color.*—Violet-red.

D. Reproductive organs:
*Androecium.*—Yellow.
*Gynoecium.*—Five part.

E. Spring flowering respnse period: Medium early.

G. Durability: Very good.

PLANT

A. Foliage:
*Form.*—Zygomorphic with a nectar spur.
*Margin.*—Crenate with spaced indentations.
*Color (upper surface).*—Medium green.
*Tolerance of botrytis and soil fungi.*—Excellent.

B. General appearance and form:
*Internode length.*—Very short.
*Branching pattern.*—Excellent.
*Height.*—Very compact.

I claim:

1. A new and distinct cultivar of geranium named Micky, as described and illustrated, and particularly characterized by its bright red-purple flower color with a much deeper red-purple variegation on the upper two petals and approximate center of lower petals; medium early flowering; good bud production at night temperatures up to 16° C., thus providing a long and continuous flowering period; very compact, self-branching growth habit; good resistance against white fly; and by its ease of propagation and rooting habit.

* * * * *

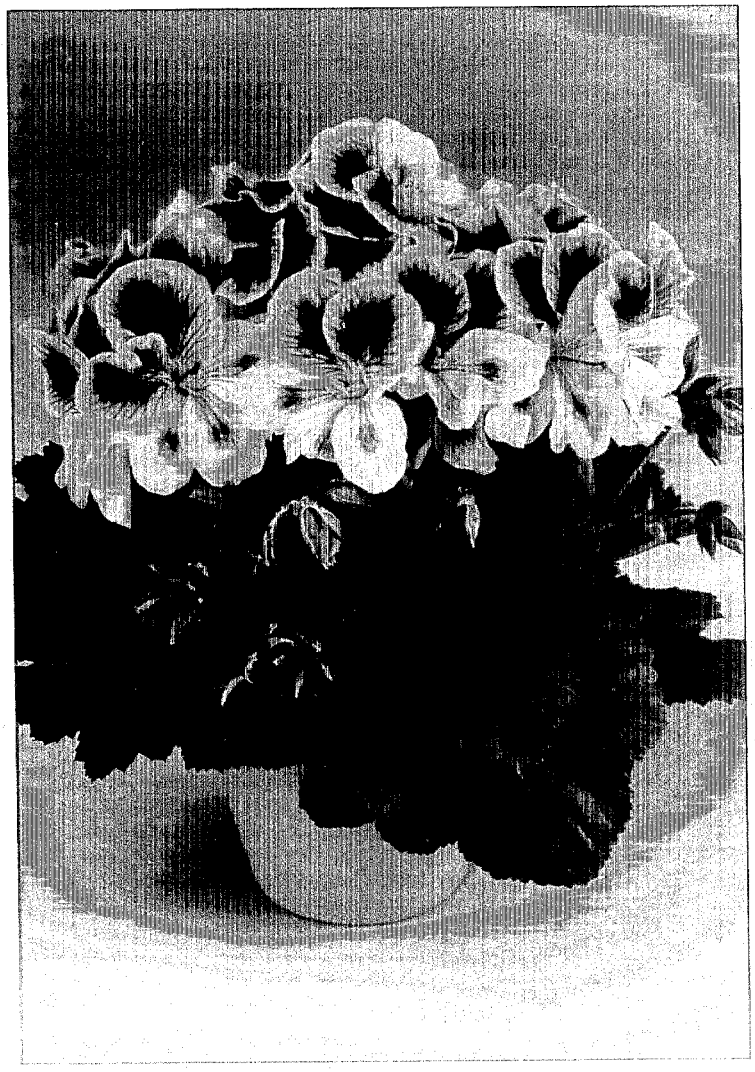

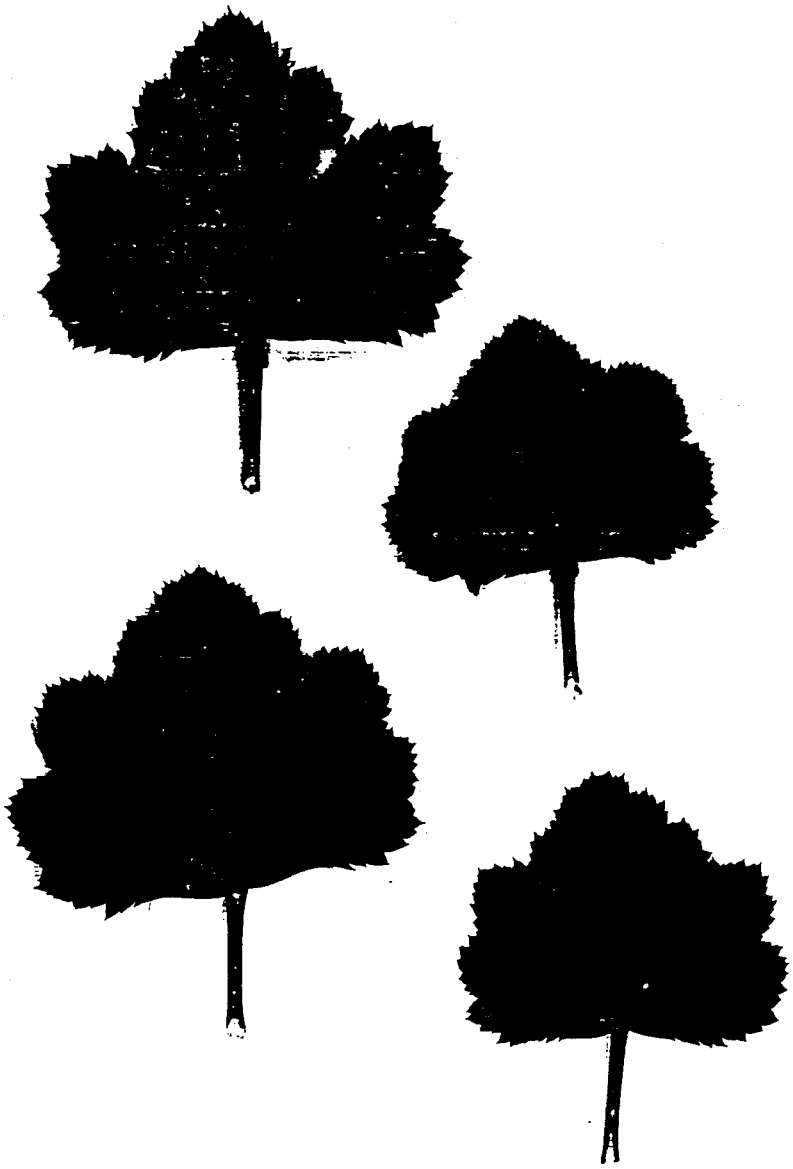

Micky